(12) United States Patent
Fukuda et al.

(10) Patent No.: US 7,888,516 B2
(45) Date of Patent: Feb. 15, 2011

(54) TGF-β GENE EXPRESSION INHIBITOR

(75) Inventors: Noboru Fukuda, Tokyo (JP); Takahiro Ueno, Tokyo (JP); Hiroshi Sugiyama, Kyoto (JP)

(73) Assignees: Nihon University, Tokyo (JP); Gentier Biosystems Incorporation, Tokyo (JP)

( * ) Notice: Subject to any disclaimer, the term of this patent is extended or adjusted under 35 U.S.C. 154(b) by 965 days.

(21) Appl. No.: 11/658,475

(22) PCT Filed: Aug. 2, 2005

(86) PCT No.: PCT/JP2005/014079

§ 371 (c)(1),
(2), (4) Date: Apr. 25, 2007

(87) PCT Pub. No.: WO2006/018967

PCT Pub. Date: Feb. 23, 2006

(65) Prior Publication Data

US 2008/0255368 A1    Oct. 16, 2008

(30) Foreign Application Priority Data

Aug. 18, 2004    (JP) .............................. 2004-238533

(51) Int. Cl.
C07D 233/00    (2006.01)

(52) U.S. Cl. .................................... 548/313.1
(58) Field of Classification Search ................. None
See application file for complete search history.

(56) References Cited

U.S. PATENT DOCUMENTS

| | | | |
|---|---|---|---|
| 6,566,336 B1 | 5/2003 | Sugiyama et al. | |
| 6,974,668 B1 | 12/2005 | Sugiyama et al. | |
| 2004/0171799 A1 | 9/2004 | Sugiyama et al. | |
| 2008/0103187 A1 | 5/2008 | Fukuda et al. | |

FOREIGN PATENT DOCUMENTS

| | | |
|---|---|---|
| JP | 2001-159768 B1 | 5/2000 |
| JP | 2000-159768 A | 6/2000 |
| JP | 2001-136974 A | 5/2001 |
| WO | WO-97/30975 A | 8/1997 |
| WO | WO-98/49142 A | 11/1998 |
| WO | WO-00/15641 A1 | 3/2000 |
| WO | WO-03/000683 A1 | 1/2003 |
| WO | WO-2005/023248 A | 3/2005 |

OTHER PUBLICATIONS

White et al., Chemistry & Biology, vol. 4, No. 8, 569-578, (1997).*
Chemistry & Biology, vol. 4, No. 8,569-578, (1997)—Applicant's IDS.*
Hiroyuki Matsuda et al., Folia endocrinologica Japanica, 2003, vol. 79, No. 1, p. 134, ISR.
Fukuda, N. Nichidai Igaku Zasshi, Jul. 2003, vol. 62, No. 7, pp. 329 to 336, ISR.
Murthy et al., "Biology of N-methylpyrrole-N-methylimidazole hairpin polyamide" Biological & Pharmaceutical Bulletin, vol. 27, No. 4, Apr. 2004, pp. 468-474, XP007907309, ISSN: 0918-6158.
Dervan et al., "Recognition of the DNA minor groove by pyrrole-imidazole polyamides" Current Opinion in Structural Biology, vol. 13, No. 3, Jun. 2003, pp. 284-299, XP002516157, ISSN: 0959-440X.
Melander et al., "Regulation of gene expression with pyrrole-imidazole polyamides" Journal of Biotechnology, Elsevier NL, vol. 112, No. 1-2, Aug. 4, 2004, pp. 195-220, XP007907307.
Heckel et al., "U-pin polyamide motif for recognition of the DNA minor groove" Chemistry (Weinheim An Der Berhstrasse, Germany) vol. 9, No. 14, Jul. 21, 2003, pp. 3353-3366, XP007907315, ISSN: 0947-6539.
Matsuda et al., "Development of synthetic pyrrole-imidazole polyamide targeting TGF-BETA.1 as a novel gene therapy for vascular proliferative diseases and progressive renal diseases" Circulation Journal, Japanese circulation Society, Kyoto, JP, vol. 68, Suppl. 1, 2004, p. 501, XP009112649, ISSN: 1346-9843.
Peik et al., "Specificity, Diversity, and Regulation in TGF-B Superfamily Signaling", 1999 FASEB J, 13, pp. 2105-2124.
Trauger et al. "Recognition of DNA by Designed Ligands at Subnanomolar Concentrations", Nature. vol. 382: pp. 559-561 Aug. 8, 1996.
White et al. "On the Pairing Rules for Recognition in the Minor Groove of DNA by Pyrrole-Imidazole Polyamides" Chemistry & Biology, 4: pp. 569-578 Aug. 1997.
Dervan. "Molecular Recognition of DNA by Small Molecules" Bioorganic & Medical Chemistry. 2001; 9: pp. 2215-2235.
White et al. "Recognition of the Four Watson-Crick Base Pairs in the DNA Minor Groove by Synthetic Ligands" Nature. Jan. 29, 1998; vol. 391 pp. 468-471.
Gottesfeld et al. "Regulation of Gene Expression by Small Molecules" Nature. May 8, 1997; vol. 387: pp. 202-205.
Dickinson et al: "Inhibition of RNA Polymerase II Transcription in Human Cells by Synthetic DNA-Binding Ligands", Proceedings of the National Academy of Sciences of the United States America. Oct. 27, 1998; vol. 95: pp. 12890-12895.
Lee et al. "Inhibition of the Association of RNA Polymerase II with the Preinitiation Complex by a Vrial Transcriptional Repressor", Proceedings of the National Academy of Sciences of the United States America. Mar. 19, 1996; vol. 93: pp. 2570-2575.

(Continued)

Primary Examiner—Cecilia Tsang
Assistant Examiner—Thomas S Heard
(74) Attorney, Agent, or Firm—Birch, Stewart, Kolasch & Birch, LLP.

(57) ABSTRACT

A TGF-β gene expression inhibitor containing a pyrrole-immidazole polyamide comprising an N-methylpyrrole unit (hereinafter also referred to as Py), an N-methylimidazole unit (hereinafter also referred to as Im) and a γ-aminobutyric acid unit which can be folded into an U-shaped conformation at the above-described γ-aminobutyric acid unit site in a minor groove of a double-stranded region (hereinafter referred to as the target region) containing a part or the whole of the following base sequence (SEQ ID NO: 2) corresponding to −450 to −310 of human transforming growth factor β1 (hereinafter also referred to as h TGF-β1) promoter and a strand complementary thereto and in which a Py/Im pair, an Im/Py pair and a PY/Py pair correspond respectively to a C-G base pair, a G-C base pair and an A-T base pair and a T-A base pair.

3 Claims, 3 Drawing Sheets

OTHER PUBLICATIONS

Dickinson et al: "Anit-repression of RNA Polymerase II Transcription by Pyrrole-Imidazole Polyamides", Biochemistry. 1999; vol. 38: pp. 10801-10807.

Mapp et al: "Activation of Gene Expression by Small Molecule Transcription Factors", Proceedings of the National Academy of Sciences of the United States America. Apr. 11, 2000; vol. 97: pp. 3930-3935.

Matsuda et al., Nihon Naibumpi Gakkai Zasshi, 2003, vol. 79, No. 1, pp. 134.

Fukuda. "Gene Therapy for Arterial Proliferative Diseases and Progressive Renal Diseases by Nucleic Acid Medicines", J. Nihon Univ. Med. Ass. (Nichidai Igaku Zasshi), 2003; 62 (7): pp. 329-336.

* cited by examiner

FIG. 1

HUMAN TGFβ PROMOTER

```
-592 ACAGGAGGCTGCTTAGCCACATGGGAGGTGCTCAGTAAAGGAGAGCAATTCTTACAGGTGTCTGCCTCCT
                                              FSE2              BBp1101
-522 GACCCTTCCATCCCTCAGGTGTCCTTGTTGCCCCCTCCCACTGACACCCTCCGGAGGCCCCATGTTG
-452 ACAGACCCCTCCTCCTTCTCCTACCTTGTTCCCAGCTGACTCTCCGTTCCGTTCTGGGTCCCCCTCTGGT
                                                     PMA   GBP1105
-382 CGGCTCCCCTGTGTCTCATCCCCGGATTAAGCCTTCTCCGCCTGGTCCTTCTTTCTCTGGTGACCACAC
      PMA  GBP1106
-312 CGCCCGCAAAGCCACAGCGCATCTGGATCACCCGCTTTGGTGGCGCTTGGCCGCCAGGAGGCAGCACCCT
                                                         NF1    GBP1107
-242 GTTTGCGGGGCGAGCGCGGGGAGCCCGCCCCCTTTCCCCAGGGCTGAAGGACCCCCCTCGGAGCCCGC
-172 CCACGCGAGATGAGGACGGTGCCCAGCCCCCCCCCCCCTGGGGCCGCCCCCCGCTCCCGCCC
-102 CGTGCGCTTCCTGGGTGGGGCCGGGGGCGGCTTCAAAACCCCTGCCGACCCCAGCCGGTCCCCGCCGCCG
                GBP1102
 -32 CCGCCCTTCGCGCCCCTGGGCCATCTCCCTCCCACCTCCCCGCGAGCAGCCAGACAGCGAGGGCCCCG
                              GBP1103
                                   *     +1
 +39 GCCGGGGGCAGGGGACGCCCCGTCCGGGGACCACCCCCCCCCCGGCTCTGAGCCGCCCGGGGGCCGGCCTCG
+109 GCCCGGAGCGGAGGAAGGAGTCGCCGAGGAGCAGCCTGAGGCCCCAGAGTCTGAGACGAGCCGCCGCCGC
+179 CCCCGCCACTGCGGGAGGAGGGGAGGAGGAGGACGAGCTGGTCGGGAGAAGAGGAAAA
                                                                          SERIES 1
                                                                          SERIES 2
                                                                          HUMAN/RAT HOMOLOGOUS REGION
                                                                          SERIES 3
                                                                          TRANSCRIPTION FACTOR
                                                                          BINDING SITE
+249 AAACTTTTGAGACTTTTCCGTGCCGCTGGGAGCCGGAGCGCGGGGACCCTCTTGGCCGACGCTGCCCC
     GBP1104     +271
```

* MAIN TRANSCRIPTION INITIATION SITE
UNDER LINE : TRANSCRIPTION FACTOR BINDING SITE
BROKEN LINE : POSSIBLE TRANSCRIPTION FACTOR BINDING SITE

FIG. 3
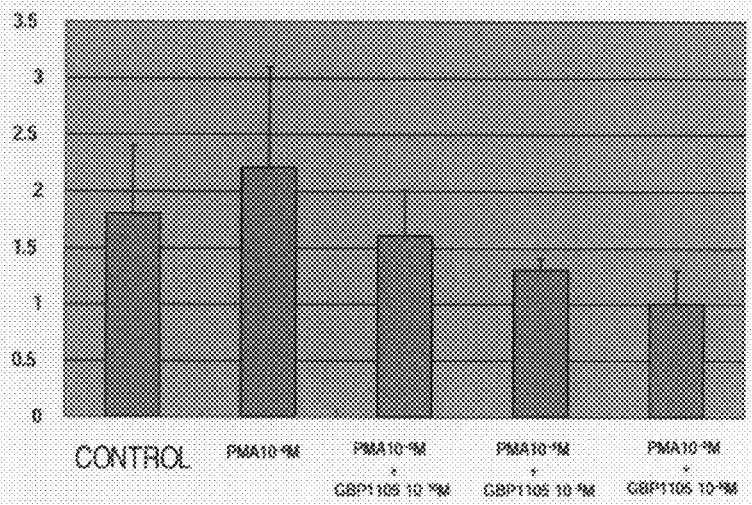
FIG. 4
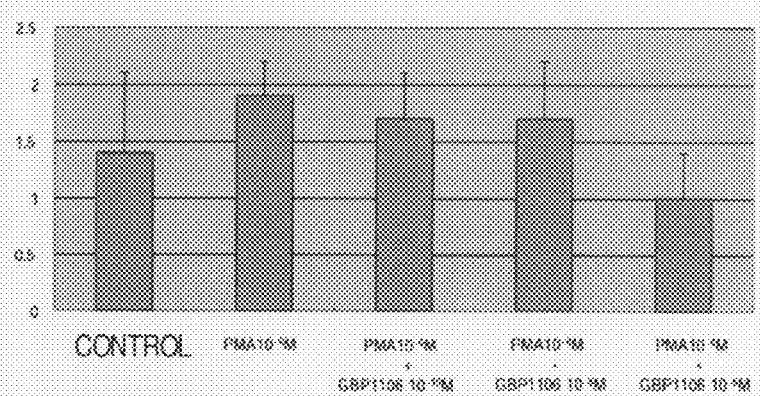
FIG. 5

SEQUENCE LISTING

```
<160> NUMBER OF SEQ ID NOS: 10

<210> SEQ ID NO 1
<211> LENGTH: 910
<212> TYPE: DNA
<213> ORGANISM: Homo sapiens
<220> FEATURE:
<221> NAME/KEY: promoter
<222> LOCATION: (1)..(592)

<400> SEQUENCE: 1
acaggaggct gcttagccac atgggaggtg ctcagtaaag gagagcaatt cttacaggtg      60
tctgcctcct gacccttcca tccctcaggt gtcctgttgc cccctcctcc cactgacacc     120
ctccggaggc cccatgttg acagaccctc cttctcctac cttgtttccc agcctgactc      180
tccttccgtt ctgggtcccc ctcctctggt cggctcccct gtgtctcatc ccccggatta     240
agccttctcc gcctggtcct cttttctctgg tgacccacac cgcccgcaaa gccacagcgc    300
atctggatca cccgctttgg tggcgcttgg ccgccaggag gcagcaccct gtttgcgggg     360
cggagccggg gagcccgccc cctttccccc agggctgaag ggacccccct cggagcccgc     420
ccacgcgaga tgaggacggt ggcccagccc ccccatgccc tccccctggg ggccgccccc     480
gctcccgccc cgtgcgcttc ctgggtgggg ccggggggcgg cttcaaaacc ccctgccgac    540
ccagccggtc cccgccgccg ccgcccttcg cgccctgggc catctccctc ccacctccct    600
ccgcggagca gccagacagc gagggccccg gccggggca gggggacgc cccgtccggg       660 gcaccccccc ggctctgagc cgcccgcggg gccggcctcg gcccggagcg gaggaaggag     720
tcgccgagga gcagcctgag gccccagagt ctgagacgag ccgccgccgc cccgccact     780 gcggggagga gggggaggag gagcgggagg agggacgagc tggtcgggag aagaggaaaa     840
aaacttttga gacttttccg ttgccgctgg gagccggagg cgcggggacc tcttggcgcg     900
acgctgcccc                                                            910

<210> SEQ ID NO 2
<211> LENGTH: 141
<212> TYPE: DNA
<213> ORGANISM: Homo sapiens

<400> SEQUENCE: 2
agaccctcct tctcctacct tgtttcccag cctgactctc cttccgttct gggtccccct      60
```

```
cctctggtcg gctccctgt gtctcatccc ccggattaag ccttctccgc ctggtcctct    120
ttctctggtg acccacaccg c                                              141

<210> SEQ ID NO 3
<211> LENGTH: 7
<212> TYPE: DNA
<213> ORGANISM: Homo sapiens

<400> SEQUENCE: 3 actctcc                                                              7

<210> SEQ ID NO 4
<211> LENGTH: 8
<212> TYPE: DNA
<213> ORGANISM: Homo sapiens

<400> SEQUENCE: 4 tgtgtctc                                                             8

<210> SEQ ID NO 5
<211> LENGTH: 31
<212> TYPE: DNA
<213> ORGANISM: Homo sapiens

<400> SEQUENCE: 5
tgtttcccag cctgactctc cttccgttct g                                   31

<210> SEQ ID NO 6
<211> LENGTH: 31
<212> TYPE: DNA
<213> ORGANISM: Homo sapiens

<400> SEQUENCE: 6
gctcccctgt gtctcatccc ccggattaag c                                   31

<210> SEQ ID NO 7
<211> LENGTH: 24
<212> TYPE: DNA
<213> ORGANISM: Artificial Sequence
<220> FEATURE:
<223> OTHER INFORMATION: Synthetic sense primer used for PCR
      amplification of hTGF-Beta1 mRNA

<400> SEQUENCE: 7
atcagagctc cgagaagcgg tacc                                           24

<210> SEQ ID NO 8
<211> LENGTH: 22
<212> TYPE: DNA
<213> ORGANISM: Artificial Sequence
<220> FEATURE:
<223> OTHER INFORMATION: Synthetic antisense primer used for PCR
      amplification of hTGF-Beta1 mRNA

<400> SEQUENCE: 8
gtccacttgc agtgttatcc tg                                             22

<210> SEQ ID NO 9
<211> LENGTH: 20
<212> TYPE: DNA
<213> ORGANISM: Artificial Sequence
<220> FEATURE:
<223> OTHER INFORMATION: Synthetic sense primer directed to human 18S
      ribosomal RNA
```

-continued

```
<400> SEQUENCE: 9
tcaagaacga aagtcggacg                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic antisense primer directed to human
      18S ribosomal RNA

<400> SEQUENCE: 10
ggacatctaa gggcatcaca                                                 20
```

TGF-β GENE EXPRESSION INHIBITOR

TECHNICAL FIELD

The present invention relates to a transforming growth factor (TGF-β) gene expression inhibitor and a therapeutic agent for diseases associated with TGF-β. More specifically, the present invention relates to a TGF-β gene expression inhibitor including a pyrrole-imidazole polyamides having a specific structure.

BACKGROUND ART

Essential hypertension causes severe complications such as apoplexy, ischemic heart diseases and nephrosclerosis. These complications are fundamentally associated with vascular disorders by excessive proliferation of vascular smooth muscle cells (VSMC), and are the targets of the treatment of hypertension. On the other hand, restenosis of coronary arteries takes place in about 40% after percutaneous transluminal coronary angioplasty (PTCA) as a treatment of angina pectoris and myocardial infarction, and further in about 30% after stent implantation. Histopathologically, TGF-β has been known to be involved in artery proliferative disorders such as hypertension vascular disease, neointimal formation after anigioplasty and in-stent neointimal formation, and atherosclerosis. Cell growth in such diseases can be inhibited by various action mechanisms, and one of them is to inhibit the expression of TGF-β.

Initially, TGF was found as a factor to change a normal cell to malignant one in mouse 3T3 cells that had been transformed by Molony sarcoma virus (MSV), and is roughly classified into TGF-α and TGF-β. TGF-β is a part composed of 112 amino acids at C-terminal side of a protein having a molecular weight of about 40,000 composed of 390 to 412 amino acids synthesized as a precursor, and that part forms a dimer (25 kDa) through disulfide-bond to have an activity.

TGF-β constitutes one family of protein that regulates the growth and development of cells (Non-patent Document 1). TGF-β is produced in various tissues such as blood vessel, platelet, liver, kidney, heart muscle, lung, pancreas, skin, placenta, and bone marrow, and has actions of cell growth, extracellular matrix formation, and immunity regulation.

TGF-β works on most cells to inhibit the growth, but has a biphasic growth action to mesenchymal cells such as fibroblast and vascular smooth muscle cell (VSMC). In other words, in these cells, TGF-β usually works to inhibit the growth but works to stimulate the growth when inflammation, mechanical stress or the like is given. These findings show that TGF-β is involved in neointimal formation after vascular injury by facilitating VSMC proliferation and extracellular matrix formation with increases in fibronectin and collagen. TGF-β is also involved in the formation of focus of arterial sclerosis. Based on the information, it is considered that local vascular therapy directed to the regulation of TGF-β effect is effective to alleviate the above vascular proliferative diseases.

Further, it is considered that TGF-β is involved in restenosis of renal artery after percutaneous transluminal renal artery angioplasty. From these facts, a TGF-β gene expression inhibition drug of the present invention is effective as a therapeutic agent to patients with the above various vascular proliferation/stenosis diseases.

Methods for inactivating gene functions by reverse genetics are used for analyzing a specific gene function, whereas such methods open high possibilities of therapy for other diseases based on virus infection, cancer, and abnormal genomic diseases. The inactivation of gene function can be performed at DNA level by homologous recombination or at RNA level by antisense oligodeoxynucleotide or ribozyme. However, methods using antisense oligodeoxynucleotide or ribozyme have drawbacks: limitation to target sequences; poor entry to tissues and cells; and easy degradation by nucleases.

On the other hand, unlike the nucleic acid medicines such as antisense oligodeoxynucleotide and ribozyme, it has been reported that pyrrole-imidazole polyamides (hereinafter also referred to as Py-Im polyamide) specifically recognize DNA base sequences and extracellularly control the expression of a specific gene.

Py-Im polyamides are a group of small synthetic molecules composed of the aromatic rings of the N-methylpyrrole unit (hereinafter also referred to as Py) and N-methylimidazole unit (hereinafter also referred to as Im) (Non-patent Documents 2 to 4). Py and Im are successively coupled to each other so that the Py-Im polyamide can be folded to have a U-shaped conformation in the presence of γ-aminobutyric acid. In a Py-Im of the present invention, an N-methylpyrrole unit (Py), an N-methylimidazole unit (Im), and a γ-aminobutyric acid unit (also referred to as γ linker) are bound to each other by amide bond (—C(=O)—NH—), and its general structure and production method are well known (see Patent Documents 1 to 3).

These synthetic Py-Im polyamides can bind to specific base pairs in a minor groove of double-stranded DNA with high affinity and specificity. Specific recognition of base pairs is dependent on one-to-one pair formation of Py and Im. That is, in U-shaped conformation in the minor groove of DNA, a Py/Im pair targets a CG base pair, Im/Py pair targets a GC base pair, and a Py/Py pair targets both AT and TA base pairs (Non-patent Documents 3 and 4). Recent studies have shown that the AT degeneracy can be overcome by replacing one pyrrole ring of the Py/Py pair with 3-hydroxypyrrole (Hp), and as a result of that, allowing a Hp/Py pair to preferentially bind to a T/A pair (Non-patent Document 5).

It is generally considered that transcription initiation is an important site for gene regulation. Initiation of transcription requires some transcription factors binding to specific recognition sequences in the gene promoter region. Py-Im polyamides designed to target the transcription factor binding site block the binding of the transcription factors and inhibit the gene expression, if the transcription factors are important for the gene expression. These principles have been proved by in vitro and in vivo experiments. An eight-ring Py-Im polyamide that bound in the recognition site of zinc finger (TFIIIA binding site) inhibited the transcription of 5S RNA genes (Non-patent Document 6). Polyamides that bind to base pairs adjacent to transcription factor sequences in a human immunodeficiency virus 1 type (HIV-1) promoter inhibits the replication of HIV-1 in a human cell. These sequences include a TATA box, a lymphoid enhancer factor LEF-1 sequence, and an ETS-1 sequence (Non-patent Document 7). In contrast, Py-Im polyamides also block a repressor factor or replace an inherent transcription factor, and thereby activate gene expression (Non-patent Documents 8 to 10). Human cytomegalovirus (CMV) UL122 mediate early protein 2 (IE86) blocks the replenishment of RNA polymerase II to a promoter to suppress the transcription of its related gene (Non-patent Document 8). Synthetic Py-Im polyamides block the suppression of IE86 and liberate the expression of the corresponding gene (Non-patent Document 9). A polyamide designed by Mapp et al. works as an artificial transcription factor and mediates gene transcription reaction (Non-patent Document 10).

Patent Document 1: Japanese Patent No. 3045706
Patent Document 2: JP-A-2001-136974
Patent Document 3: WO 03/000683 A1
Non-patent Document 1: Piek et al., FASEB J, 13, 2105-2124 (1999)
Non-patent Document 2: Trauger et al: Nature. 1996; 382: 559-61
Non-patent Document 3: White et al: Chem. Biol., 1997; 4: 569-78

Non-patent Document 4: Dervan: Bioorg Med. Chem. 2001; 9: 2215-35

Non-patent Document 5: White at al: Nature. 1998; 391: 468-71

Non-patent Document 6: Gottesfeld et al: Nature. 1997; 387: 202-5

Non-patent Document 7: Dickinson et al: Proc Natl Acad Sci USA. 1998; 95: 12890-5

Non-patent Document 8: Lee et al: Proc Natl Acad Sci USA. 1996; 93: 2570-5

Non-patent Document 9: Dickinson et al: Biochemistry. 1999; 38: 10801-7

Non-patent Document 10: Mapp et al: Proc Natl Acad Sci USA. 2000; 97: 3930-5

DISCLOSURE OF THE INVENTION

Problem to be Solved by the Invention

A method using antisense oligodeoxynucleotide or ribozyme as described above has drawbacks: limitation to target sequences; poor entry to tissues and cells; and easy degradation by nucleases. There has been so far no report on a TGF-β gene expression inhibitor or a therapeutic agent for TGF-β related diseases using Py-Im polyamide that binds to a base sequence of hTGF-β gene.

Means for Solving the Problem

The present inventors have made intensive studies on the development and pharmacological effects of Py-Im polyamide that can inhibit the expression of human TGF-β gene by specifically binding to a specific region of a promoter of human TGF-β (hTGF-β1). In order to obtain a compound that can inhibit the expression of hTGF-β1 gene and be useful as a therapeutic agent, the present inventors have found a compound that binds to a region including AP1 binding region of −450 to −310 of a promoter region, preferably a region of −430 to −400 or a region of −380 to −350, more preferably a region of −416 to −410 or a region of −373 to −366, from polyamides targeting various fragments of an hTGF-β1 promoter, and the compound significantly inhibits the activity of the hTGF-β1 promoter and suppresses expression of the hTGF-β1 gene in cultured human VSMC, thereby achieving the present invention.

Specifically, the present inventions are as described below.

(1) A TGF-β gene expression inhibitor comprising a pyrrole imidazole (Py-Im) polyamide containing an N-methylpyrrole unit (hereinafter also referred to as Py), an N-methylimidazole unit (hereinafter also referred to as Im), and a γ-aminobutyric acid unit, wherein:

the Py-Im polyamide can be folded into a U-shaped conformation at a site of the γ-aminobutyric acid unit in a minor groove of a double-stranded region (hereinafter referred to as a target region) containing a part or an entire of base sequence −450 to −310 (SEQ ID NO: 2) as shown below of an hTGF-β1 promoter and a strand complementary thereto; and a Py/Im pair, an Im/Py pair, and a Py/Py pair correspond to a CG base pair, a GC base pair, and AT and TA base pairs, respectively.

(2) The TGF-β gene expression inhibitor described in the above (1), further comprising a β-alanine unit.

(3) The TGF-β gene expression inhibitor described in the above (1) or (2), wherein the target region is a double-stranded region containing a part or an entire of base sequence −430 to −400 (SEQ ID NO: 5) as shown below of an hTGF-β1 promoter and a strand complementary thereto.

(4) The TGF-β gene expression inhibitor described in the above (1) or (2), wherein the target region is a double-stranded region containing a part or an entire of base sequence −416 to −410 (SEQ ID NO: 3) as shown below of an hTGF-β1 promoter and a strand complementary thereto.

(5) The TGF-β gene expression inhibitor described in the above (1) or (2), wherein the target region is a double-stranded region containing a part or an entire of base sequence −380 to −350 (SEQ ID NO: 6) as shown below of an hTGF-β1 promoter and a strand complementary thereto.

(6) The TGF-β gene expression inhibitor described in the above (1) or (2), wherein the target region is a double-stranded region containing a part or an entire of base sequence −373 to −366 (SEQ ID NO: 4) as shown below of an hTGF-β1 promoter and a strand complementary thereto.

(7) The TGF-β gene expression inhibitor described in any one of the above (1) to (6), wherein a carboxylic group at a terminal of the Py-Im polyamide forms an amide.

(8) The TGF-β gene expression inhibitor described in any one of the above (1) to (7), wherein the amide is an amide with methylaminopropylamine or N, N-dimethylamino-propylamine.

(9) The TGF-β gene expression inhibitor described in the above (1) to (4), wherein the Py-Im polyamide is represented by the following formula.

[Formula 1]

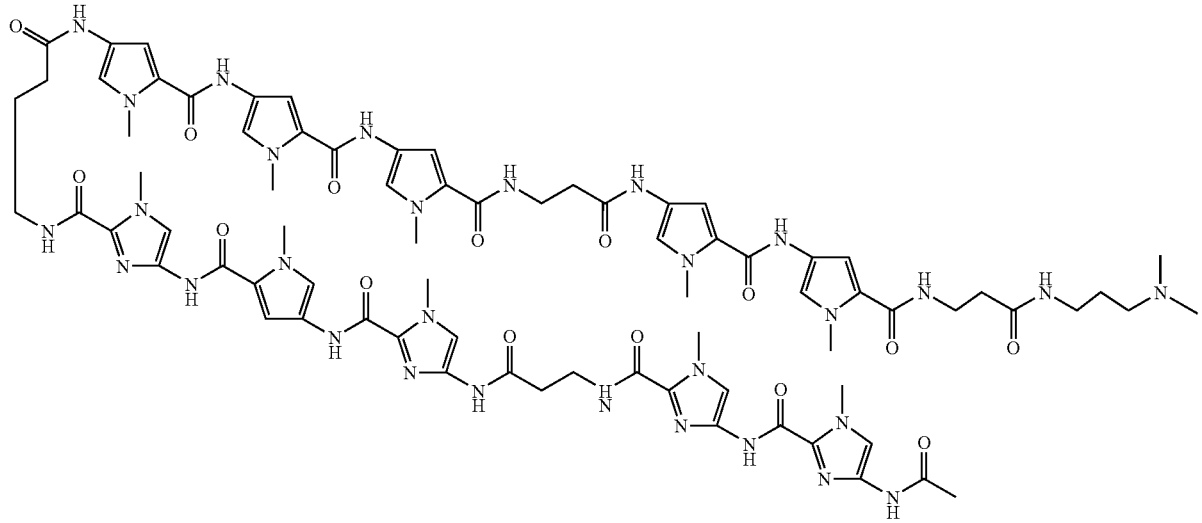

(10) The TGF-β gene expression inhibitor described in the above (1), (2), (5), or (6), wherein the Py-Im polyamide is represented by the following formula.
[Formula 2]
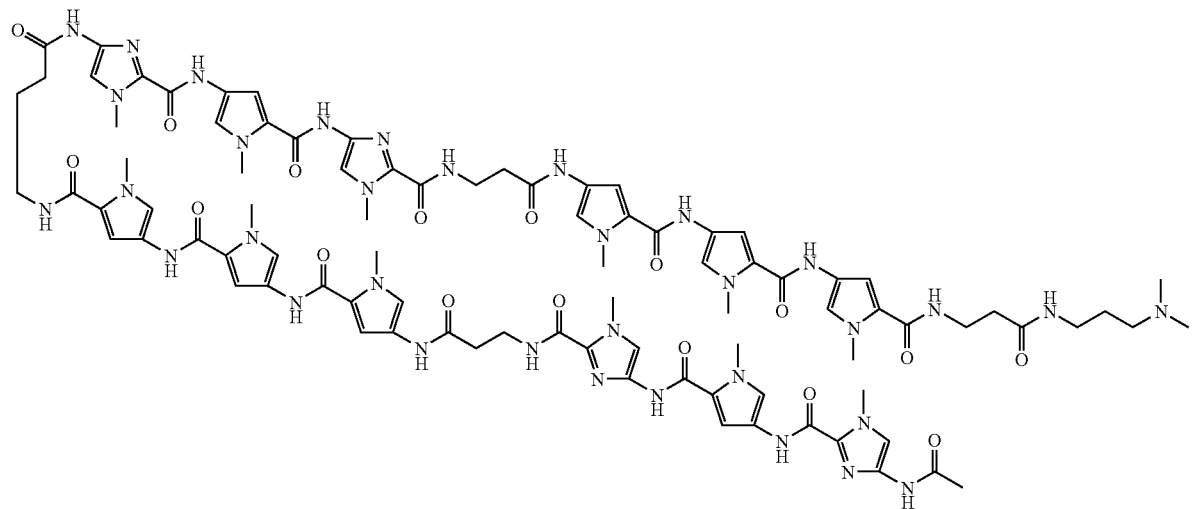
11) A Py-Im polyamide represented by the following formula:
[Formula 3]
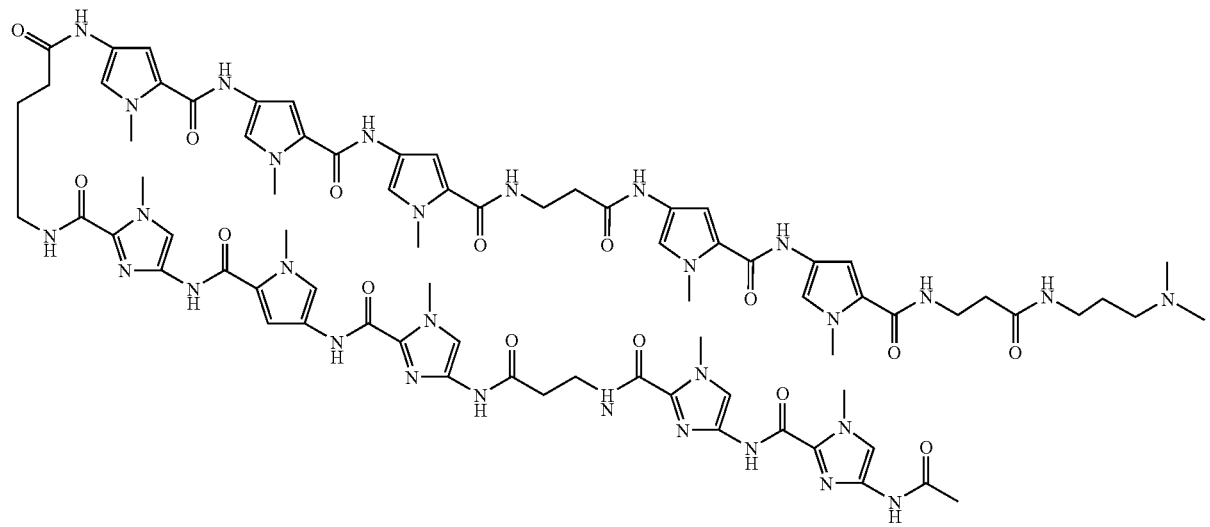
or -continued

[Formula 4]

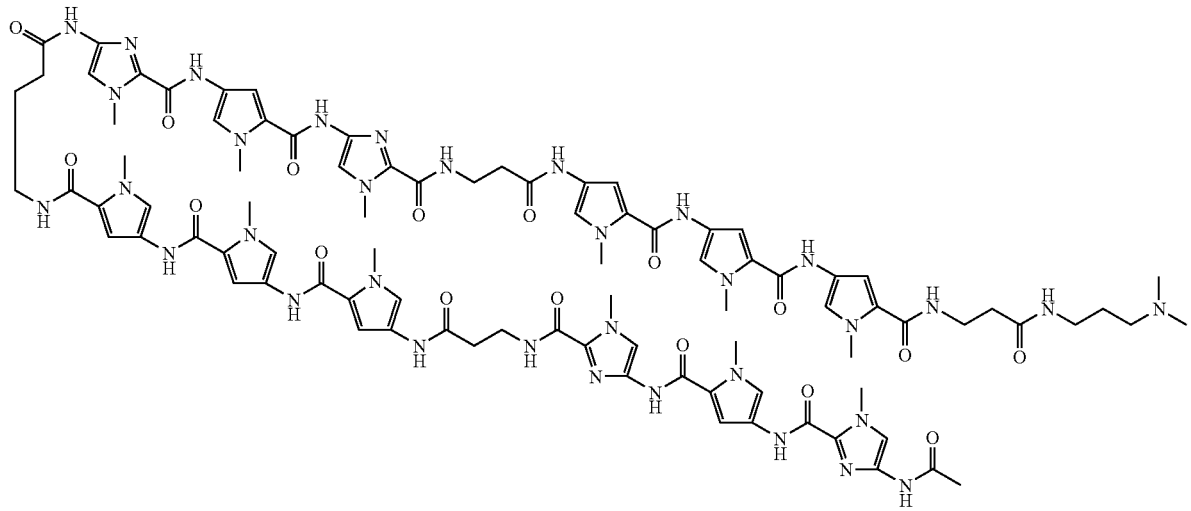

Advantages of the Invention

The present invention provides a TGF-β gene expression inhibitor that can specifically inhibit gene expression thereby to cause no side effect unlike a chemotherapeutic agent, and has no drawback that degradation of a compound is caused by nuclease.

BRIEF DESCRIPTION OF THE DRAWINGS

FIG. 1 shows a base sequence of a regulatory region of a human TGF-β1 gene (SEQ ID NO:1);

FIG. 3 shows a photograph showing gel shift assays of Py-Im polyamide-oligonucleotide complexes;

FIG. 4 is a graph showing inhibition effect of GB1105 on expression of TGF-β1 messenger RNA; and FIG. 5 is a graph showing inhibition effect of GB1106 on expression of TGF-β1 messenger RNA.

BEST MODE FOR CARRYING OUT THE INVENTION

Figure 2:
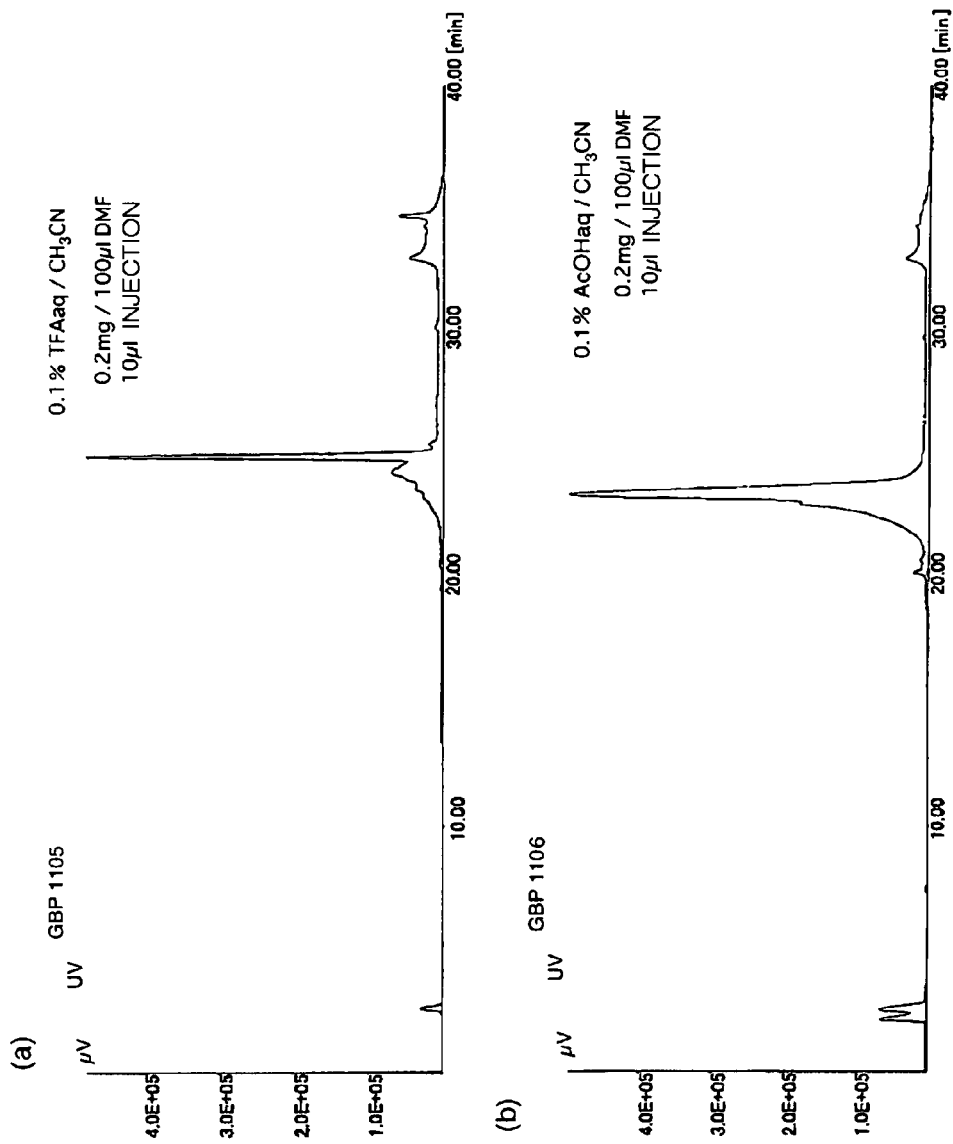
FIG. 2 shows RP-HPLC charts (a) and (b) of respective Py-Im polyamides GB1105 and GB1106 of the present invention.

In a Py-Im polyamide of the present invention, an N-methylpyrrole unit (hereinafter also referred to as Py), an N-methylimidazole unit (hereinafter also referred to as Im), and a γ-aminobutyric acid unit (also referred to as γ linker) are bound to each other by amide bond (—C(=O)—NH—), and its general structure and production method are well known (for example, see Patent Documents 1 to 3).

For example, Py-Im polyamide can be produced by an automatic synthesis method by a solid phase method (solid phase Fmoc method) using Fmoc (9-fluorenylmethoxycarbonyl) (Patent Document 3). According to the solid phase Fmoc method, it is possible to excise the terminus of Py-Im polyamide from the solid phase carrier as a carboxylic acid residue, and therefore various functional groups can be introduced into the molecular terminal, whereby derivatives of Py-Im polyamide can be produced. If necessary, it is possible to introduce, for example, duocarmycin, pyrrolo-benzodiazepin, bleomycin, enediyne compounds, nitrogen mustard, and derivatives thereof, those having DNA alkylation ability.

Since the solid phase Fmoc method is the automatic synthesis method using a commercially available protein (peptide)synthesizer, it is possible to synthesize a conjugate of a Py-Im polyamide with a naturally occurring protein or a non-natural protein. Moreover, the reaction conditions of the Fmoc method are less strict than those of the t-BOC method, and therefore it is possible to introduce organic compounds (including compounds having a functional group that is unstable under the acidic condition) other than proteins. For example, it is possible to automatically synthesize a conjugate of a Py-Im polyamide with DNA or RNA (or derivatives thereof).

According to the known Fmoc method or the like, it is possible to synthesize a Py-Im polyamide having a carboxyl group at its terminal. Specific examples thereof include Py-Im polyamides having a alanine residue (β-aminopropionic residue) or a γ-aminobutyric residue at their terminals. The Py-Im polyamide having a β-alanine residue or a γ-aminobutyric residue at its terminal can be synthesized by a peptide synthesizer by the solid phase Fmoc method, using aminopyrrole carboxylic acid, aminoimidazole carboxylic acid, and a solid phase carrier carrying β-alanine or γ-aminobutyric acid, each having an amino group protected by Fmoc.

Specific examples of the aminopyrrole carboxylic acid include 4-amino-2-pyrrole carboxylic acid, 4-amino-1-methyl-2-pyrrole carboxylic acid, 4-amino-1-ethyl-2-pyrrole carboxylic acid, 4-amino-1-propyl-2-pyrrole carboxylic acid, and 4-amino-1-butyl-2-pyrrole carboxylic acid. Specific examples of the aminoimidazole carboxylic acid include 4-amino-2-imidazole carboxylic acid, 4-amino-1-methyl-2-imidazole carboxylic acid, 4-amino-1-ethyl-2-imidazole carboxylic acid, 4-amino-1-propyl-2-imidazole carboxylic acid, and 4-amino-1-butyl-2-imidazole carboxylic acid.

According to the solid phase Fmoc method, it is possible to synthesize, for example, a conjugate of a Py-Im polyamide with FITC (fluorescein isothiocyanate). Conventionally, FITC has been known as a fluorescent labeling reagent for antibodies, and thus the obtained conjugate can be used to prove that the Py-Im polyamide recognizes a specific DNA sequence.

A TGF-β gene expression inhibitor of the present invention comprises a Py-Im polyamide containing an N-methylpyrrole unit (Py), an N-methylimidazole unit (Im), and a γ-aminobutyric unit, and the Py-Im polyamide can be folded into a U-shaped conformation at a site of the γ-aminobutyric unit in a minor groove of a double-stranded region (hereinafter referred to as target region) containing a part or an entire of base sequence −450 to −310 (SEQ ID NO: 2) of a hTGF-β1 promoter and a strand complementary thereto, in which a Py/Im pair, an Im/Py pair, and a Py/Py pair correspond to a CG base pair, a GC base pair, and AT and TA base pairs, respectively.

Usually, a skeleton of DNA helix creates two kinds of grooves, and a wide and deep groove is called major groove and a narrow and shallow groove is called minor groove. Here, the Py-Im polyamide can nonconjugatedly bind to a minor groove formed by specific base pairs with high affinity and specificity. In the bindings at this time, a Py/Im pair of Py-Im polyamide, an Im/Py pair, and a Py/Py pair correspond to a CG base pair, a GC base pair, and AT and TA base pairs, respectively, in the minor groove. Then, the molecule is folded at a site of γ-aminobutyric unit in the Py-Im polyamide molecule to have a U-shaped conformation.

If base pairs in the minor groove do not correspond to Py-Im pairs of the Py-Im polyamide as described above, the binding between the minor groove and the Py-Im polyamide becomes insufficient. A Py-Im polyamide having Py-Im pairs not corresponding to base pairs in a minor groove as described above is called mismatch or mismatch polyamide in the present application.

A base sequence of hTGF-β1 gene regulatory region is shown in FIG. 1 and in SEQ ID NO: 1 (Journal of Biological Chemistry, Vol. 264, No. 1, 402-408 (1989)).

Py-Im polyamide, GB1105 and GB1106, of the present invention are as shown below.

[Formula 5]

GB1105

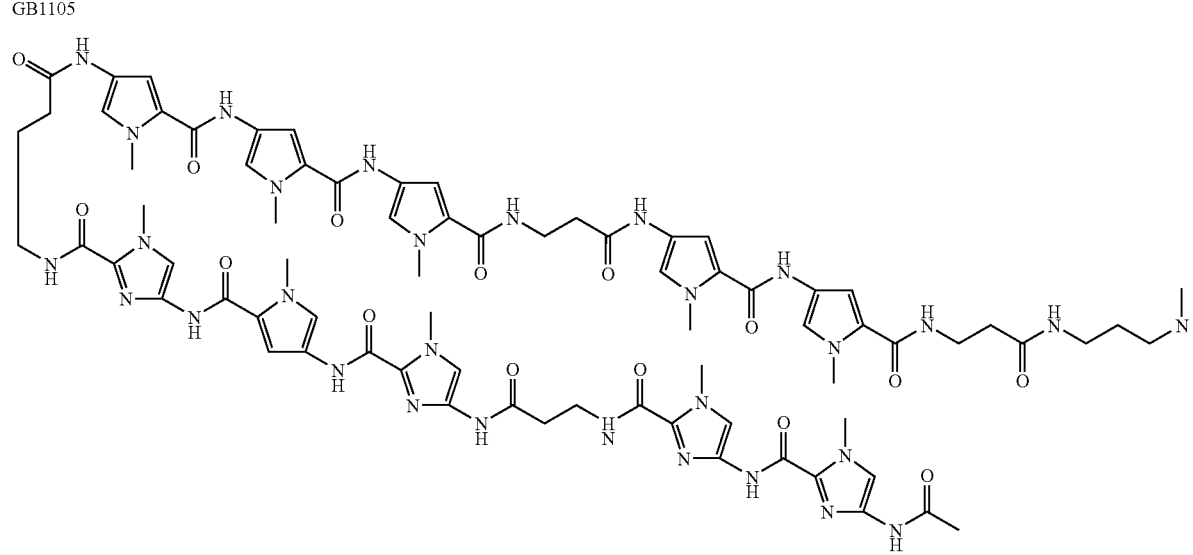

$C_{76}H_{94}N_{30}O_{15}$
Exact Mass: 1666.75
Mol. Wt.: 1667.75
C, 54.73; 5.68; N, 25.20; O, 14.39 or

[Formula 6]

GB1106

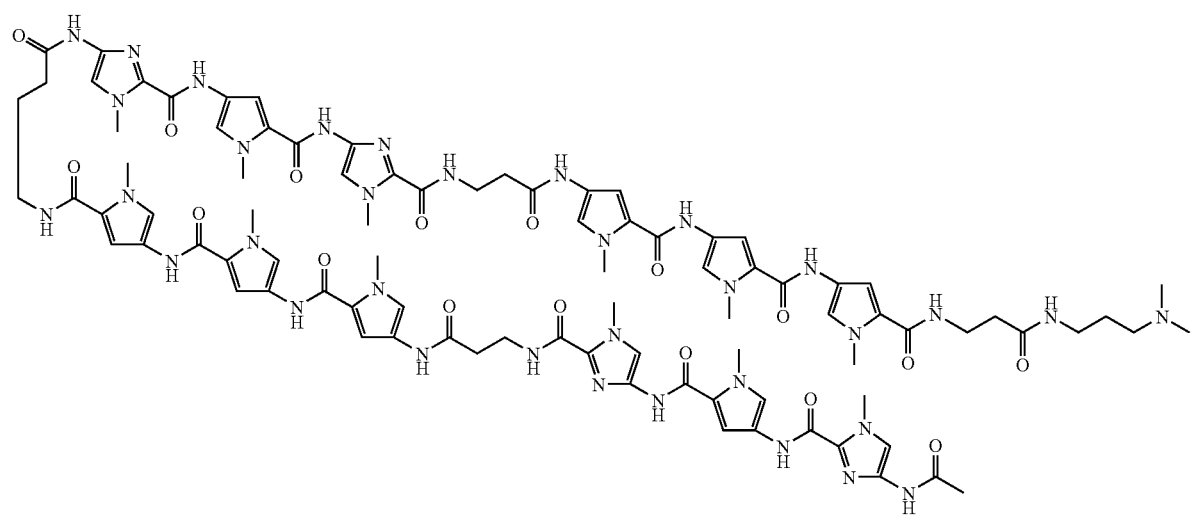

$C_{88}H_{106}N_{34}O_{17}$
Exact Mass: 1910.85
Mol. Wt.: 1912.00

GB1105 has a molecular formula $C_{76}H_{94}N_{30}O_{15}$ and a molecular weight of 1667.75, and its target sequence is a region of −430 to −400 (SEQ ID NO: 5) including AP1 binding region among a region of −450 to −380 of hTGF-β1 gene regulatory region. More specifically, the binding of GB1105 to 7 bases of gactctc (−416 to −410) (SEQ ID NO: 3) inhibits the expression of hTGF-β1 gene.

GB1106 has a molecular formula $C_{88}H_{106}N_{34}O_{17}$ and a molecular weight of 1912.00, and its target sequence is a region of −380 to −350 (SEQ ID NO: 6) including AP1 binding region among a region of −380 to −310 of hTGF-β1 gene regulatory region. More specifically, the binding of GB1106 to 8 bases of tgtgtctc (−373 to −366) (SEQ ID NO: 4) inhibits the expression of hTGF-β1 gene.

Py-Im polyamide is an effective inhibitor or activator on a general or tissue-specific transcription factor in in vitro researches (Non-patent Document 6 to 10). When *Drosophila* was grown with a specific polyamide, it obtained or lost a functional phenotype without toxicity. This was a result obtained by specifically controlling gene expression with the polyamide (Janssen et al: Mol. Cell. 2000; 6: 1013-24, Janssen at al: Mol. Cell. 2000; 6: 999-1011). The present inventors synthesized Py-Im polyamides targeting a specific region of an hTGF-β1 promoter. These polyamides stably remained in the nucleus for 48 hours or more especially without elimination thereof. In comparison with antisense oligonucleotide and ribozyme, the Py-Im polyamide has exhibited more excellent permeability (low concentration, no transfection medium) and higher stability in cultured hVSMC. High permeability and stability of polyamide provide an ideal pharmaceutical approach to the nucleus of eukaryotic cell for gene therapy.

Until recently, Py-Im polyamide development was based on structural characteristic of transcription factor-DNA complex in a promoter sequence. An effective method for targeting a sequence in a TATA box-containing promoter is to design a polyamide to bind to base pairs adjacent to the TATA box. TATA box is located at upstream 25 to 35 base pairs of the transcription initiation site in most protein-coding genes. Transcription mediate factor D ($TAF_{II}D$) includes TATA box-binding protein (TBP) that specifically binds to the TATA box, and other transcription-involved factor in a core promoter is adopted to form a pre-initiation complex (PIC). PIC initiates gene transcription and has interaction with an activator or a suppressor to regulate gene expression. Since TBP also binds to a minor groove of a double-stranded DNA (Lee et al: Cell. 1991 Dec. 20; 67(6): 1241-50, Starr et al: Cell. 1991; 67: 1231-40, Courey et al: Cell. 1988; 55: 887-98), synthetic polyamides competitively occupy binding site of the TATA binding protein to interfere with gene transcription. Among successful examples of Py-Im polyamides designed by various promoters, it is known that polyamides targeting the TATA box always function (Non-patent Documents 7 and 8).

There are some kinds of promoters that do not include the TATA box and an initiator region (Inr) (Javahery et al: Mol Cell Biol. 1994; 14: 116-27; Lo et al: Gene. 1996 Dec. 5; 182(1-2): 13-22; Romeo et al: Gene. 1997; 189: 289-95). Highly expressed and specialized gene promoter tends to have a TATA box, but a promoter of a housekeeping gene tends to lack it. A promoter without TATA may be necessary for a gene expressed at a low level or a gene requiring strict down-regulation during growth, but further researches on its mechanism are needed from now on. An hTGF-β1 promoter belongs to this kind. This includes several positive and negative sequences in various upstream region of the transcription initiation site (Kim et al: J Biol. Chem. 1989; 264: 402-8).

Several SP-1 sequences and two AP-1 sequences are present adjacent to the transcription initiation site. Since various viral and cellular promoters are activated by the SP-1 protein, a single SP-1 sequence seems to be sufficient to stimulate the promoter (Kadonaga et al: Cell. 1987; 51: 1079-90, Courey et al: Cell. 1988; 55: 887-98). The AP-1 sequence responds to an AP-1 transcription factor composed of any of Jun homodimer or Fos/Jun heterodimer complex. Through the AP-1 sequence, several substances such as 12-O-tetradecanoylo-phorbol-13-acetate (TPA), v-src gene product, and hTGF-β1 itself stimulates the expression of hTGF-β1 gene (Kim et al: J Biol. Chem. 1989; 264: 7041-5, Kim et al: J Biol. Chem. 1989; 264: 19373-8, Kim et al: Mol Cell Biol. 1990; 10: 1492-7, Birchenall-Roberts et al: Mol Cell Biol. 1990; 10: 4978-83).

SP-1 and/or AP-1 sequence mediate activation of hTGF-β1 gene expression. Since a Py-Im polyamide blocks the binding of a responsive transcription factor, the Py-Im polyamide is designed to target base pairs adjacent to different AP-1 and SP-1 sequence. However, there is no sufficient data indicating that these Py-Im polyamides can inhibit the activity of hTGF-β1 promoter or activate the hTGF-β1 promoter. These results may be obtained since designed Py-Im polyamides occupied inappropriate locations in the minor groove of DNA, etc. The present inventors extended the target sequence to the upstream of hTGF-β1 promoter. One polyamide targeted an hTGF-β1 promoter, and this has demonstrated the inhibition of promoter activity in vitro and the inhibition of hTGF-β1 mRNA and protein in cultured hVSMC. A transcription repressor to inhibit the transcription was found from a core promoter including a TATA box, but not found from a promoter including no TATA (Aso et al: EMBO J. 1994; 13: 435-45, Mack et al: Nature. 1993; 363: 281-3, Merino et al: Nature. 1993; 365: 227-32). Since the expression of most mammalian genes is likely to depend on the combined actions of numerous proteins bound to promoter and enhancer sequences, the simplest model for explaining this time results is that the Py-Im polyamide of the present invention blocks transcription factor-DNA interaction and exhibits inhibiting effect on hTGF-β1 promoter activity.

In addition to the regulation of transcription factor in promoter region, there is a possibility that other factors affect gene expression. These factors include chromatin packing, polyadenylation, splicing, mRNA stability, and translation initiation (Berger et al: Mol. Cell. 2001; 5: 263-8, McKeown Annu Rev Cell Biol. 1992; 8: 133-55, Decker et al: Trends Biochem Sci. 1994; 19: 336-40, Kozak Annu Rev Cell Biol. 1992; 8: 197-225). Synthetic Py-Im polyamides can access their target sites in accordance with positional relation of the nucleosome and may affect condensation/decondensation structure of chromatin by targeting specific sequences (Gottesfeld et al: J Mol. Biol. 2002; 321: 249-63; Gottesfeld et al: Mol. Biol. 2001; 309: 615-29). It has been proved that Py-Im polyamide induces the heterochromatic brown satellite to allow binding of GAF, resulting in a phenotypic change in *drosophila melanogaster*. Since Py-Im polyamides can be synthesized and designed to target any sequence of interest, they are useful for studies of genome function and eventually for gene therapies such as inhibition or activation of hTGF-β1 gene.

The Py-Im polyamide of the present invention can be designed at upstream distant from the transcription initiation region, and this exhibits an inhibition effect to hTGF-β1 gene expression.

Furthermore, in the process of fibrosis formation in liver cirrhosis, hepatic stellate cells play an important role in the production the extracellular matrix (Bataller R et al, Gastroenterology 118, 1149, 2000). Activation of the stellate cells is caused by TGF-β1, and further activated stellate cells induce the secretion of TGF-β1 from inflammatory cells in a damaged liver. At the same time, the expression of TGF-β1 receptor in the activated stellate cells is enhanced, and an autocrine mechanism by TGF-β1 increases extracellular matrix protein (Hisayoshi WATANABE et al., Gendai-iryo, Vol. 35, (No. 2), 2003). From these facts, it is reasonably considered that the TGF-β1 gene expression inhibitor of the present invention is effective as a therapeutic agent for the liver cirrhosis.

Furthermore, TGF-β is involved in progressive renal diseases such as IgA nephropathy, focal glomerulosclerosis, lupus nephritis, diabetic nephropathy, and hypertensive nephrosclerosis, by the increases in cellular growth, extracellular matrix and fibrosis (Yamamoto T et al: Kidney Int 49: 461, 1996; Border W A et al: Kidney Int 51: 1388, 1997). Further, Border et al. reported that administration of anti-TGF-β to Thy-1 nephritis rat inhibited accumulation of extracellular matrix in glomerulus (Border WA et al: Kidney Int 51: 1388, 1997). From these facts, it is reasonably considered that the TGF-β1 gene expression inhibitor of the present invention is effective as a therapeutic agent to the above various renal diseases.

Moreover, in animal models with myocardial infarction, the expression of TGF-β is sustainably enhanced in an infarct area at scar formation stage, and TGF-β is involved in acceleration of myocardial fibrosis (Ono et al: Circulation 98: 149, 1998). From these facts, it is reasonably considered that the TGF-β1 gene expression inhibitor of the present invention is effective as a therapeutic agent to myocardial fibrosis after myocardial infarction.

Furthermore, administration of anti-TGF-β antibodies or TGF-β soluble receptors to animal models with pulmonary fibrosis improves pulmonary fibrosis (Giri S N al: Thorax 1993). From these facts, it is reasonably considered that the TGF-β1 gene expression inhibitor of the present invention is effective as a therapeutic agent to pulmonary fibrosis.

Furthermore, there are many reports on high expression of TGF-β1 in human chronic pancreatitis. However, administration of recombinant TGF-β to animal models with recurrent acute pancreatitis caused fibrosis of inflammatory parts of pancreas or high expression of fibronectin mRNA. Meanwhile, it has been reported that administration of neutralizing antibodies of TGF-β1 in preparing models with pancreatitis inhibits the production of extracellular matrix and the expression of mRNA of I-III type collagen or fibronectin (Naohiko MAKINO et al.: Gendai-iryo, Vol. 35, No. 2, 2003). From these facts, it is reasonably considered that the TGF-β1 gene expression inhibitor of the present invention is effective as a therapeutic agent to fibrosis in chronic pancreatitis.

Moreover, TGF-β was proposed as a cause for skin fibrotic diseases such as scleroderma. Mori et al. reported that TGF-β induced dermal fibrosis in mouse models with dermal fibrosis (Mori et al.: J Cell Physiol 181: 153, 1999). From these facts, it is reasonably considered that the TGF-β1 gene expression inhibitor of the present invention is effective as a therapeutic agent to various dermal fibrosis diseases.

Furthermore, it has been reported that the expression of TGF-β mRNA was enhanced in megakaryocytes of patients with bone marrow fibrosis (Reilly J et al: Clin Haematol: 11751-767, 1998), the concentration of TGF-β in platelet was high (Martyre M C et al: Br J Haematol 77: 80-86, 991), and the concentration of TGF-β in patient plasma was significantly high (Rameshwar P et al: Am J Haematol 59: 133-142, 1998). According to Rameshwar et al., the adhesion of monocytes from patients with bone marrow fibrosis activates NF-k, which induces IL-1 production and IL-1 enhances the production of TGF-β to evoke bone marrow fibrosis (Rameshwar et al: J Immunol 165: 2271-2277, 2000). From these facts, it is reasonably considered that the TGF-β1 gene expression inhibitor of the present invention is effective as a therapeutic agent to bone marrow fibrosis.

Furthermore, it has been reported that, in cultured cell line of patients with androgenetic forehead alopecia, androgen induced TGF-β1 from dermal papilla cells and the TGF-β1 suppressed epithelial cell growth (Shigeki et al: FASEB J 16: 1967-1969, 2002). From these facts, it is reasonably considered that the TGF-β1 gene expression inhibitor of the present invention is effective as a therapeutic agent to androgenetic forehead alopecia.

EXAMPLES

I. Materials and Methods (1) Design of Py-Im Polyamide Corresponding to hTGF-β1 Promoter As Py-Im polyamide, GB1105 or GB1106 as described above was designed to bind to base pairs of −416 to −410 or −373 to −366 of an hTGF-β1 promoter.

(2) Machine-Assisted Automatic Synthesis of Py-Im Polyamide using Fmoc Method

Machine-assisted automatic synthesis of Py-Im polyamides was performed with a Pioneer™, a continuous-flow peptide synthesizer (Applied Biosystems) on a 0.1 mmol scale (200 mg of Fmoc-β-alanine-CLEAR acid resin, 0.50 meq/g, Peptide Institute, Inc.). Automatic solid phase synthesis consisted of DMF washing, removal of the Fmoc group with 20% piperidine/DMF, methanol washing, coupling with monomer in the presence of HATU and DIEA (4 equivalents each) for 60 minutes, methanol washing, protection with acetic anhydride/pyridine if necessary, and final DMF washing. In general, Py-Im polyamides were obtained at moderate yields (10% to 30%).

FITC coupling: 4 times excessive of fluorescein (0.40 mmol) and DIEA (without HATU) were dissolved in DMF and the obtained solution was passed through a column for 60-minute flash.

General procedure: after removal of Fmoc group of Fmoc-β-alanine-Wang resin, the resin was washed successively with methanol. The coupling process was performed with Fmoc amino acid followed by washing with methanol. These processes were repeated several times until all sequences were introduced. After the completion of the coupling processes, the N-terminal amino group was protected or coupled with FITC and washed with DMF, and the reaction vessel was removed.

Decomposition as carboxylic acid: synthesized polyamides were isolated after the decomposition process (5 ml of mixture containing 91% TFA-3% TIS-3% DMS-3% water/0.1 mmol resin) by cold ethyl ether precipitation.

Decomposition as amine: synthesized polyamides were isolated after the decomposition process (5 mL of N,N-dimethylamino-propylamine/0.1 mmol resin, 50° C. overnight) by cold ethyl ether precipitation.

Purification: final purification was performed with an RP-HPLC for analysis at 10 mL/min. using a linear gradient of B (acetonitril) in a buffer solution A (0.1% TFA/water or 0.1% AcOH/water) and by UV detection at 350 nm. RP-HPLC charts for GB1105 and GB1106 are shown (a) and (b) of FIG. 2, respectively.

(3) hVSMC Cell Culture hVSMC cells (Clonetics) were cultured in Dulbecco modified Eagle medium (DMEM) supplemented with 10% fetal calf serum (Invitrogen), 100 U/mL of penicillin, and 100 mg/mL streptomycin. The cells were passaged by trypsinization with 0.05% trypsin (Invitrogen) in $Ca^{2+}$- and $Mg^{2+}$-free phosphate-buffered saline (PBS) and incubated in 75-$cm^2$ tissue culture flasks. The medium was changed every 4 to 5 days, and experiments were performed on the cells after 5 to 10 passages.

(4) Incubation of FITC-Labeled Polyamides in Cultured hVSMC

The passaged hVSMC cells were incubated at a density of $10^5/cm^2$ for 24 hours in 24-well flasks. FITC-labeled polyamide was added to directly to the medium at a density of $10^{-9}$ M, and observation was performed every one hour by a fluorescence microscope.

(5) Gel Shift Assay

Oligonucleotides were synthesized and annealed, and thereby 12 types of double-stranded oligonucleotides corresponding to base pairs of an hTGF-β1 promoter were prepared. A double-strand DNA was labeled with [$\gamma$-$^{32}$P]-ATP by T4 polynucleotide kinase. The labeled double-stranded DNA was then incubated for 15 minutes at 37° C. with a polyamide or a mismatch polyamide in a binding buffer solution (40 mM Tris, pH 7.9, 250 mM NaCl, 25 mM EDTA, 25 mM DTT, 100 mM KCl). The obtained complexes were separated by electrophoresis on 20% polyacrylamide gels and visualized by autoradiography.

(6) Reverse Transcription-Polymerase Chain Reaction (RT-PCR) Assay for RNA Extraction and Growth Factor mRNA The cultured cells were washed with PBS, dissolved in 1,000 μL of Trizol (Invitrogen), mixed with 100 μL of chloroform, and centrifuged, and an upper aqueous phase thereof was mixed with an equal volume of isopropanol to precipitate RNA. The resulting RNA pellet was washed twice with 500 μL of 75% ethanol, dried, and dissolved in 10 μL of TE buffer solution. The RNA sample was denatured for 15 minutes at 65° C., and treated at room temperature for 45 minutes with 0.5 U of DNase (Gibco) in 0.5 ml of DNase buffer solution (20 mM Tris-HCl pH 8.3, 50 mM KCl, 2.5 mM $MgCl_2$. The DNase was inactivated by adding 0.5 mL of 0.5 M EDTA and heating at 98° C. for 10 minutes.

An equal volume of RNA (1 μg/20 μL) was reverse-transcribed into single-stranded cDNA by 2.5 U/20 μL of avian myeloblastoma virus reverse transcriptase (Takara Biochemicals, Osaka, Japan) in 10 mM Tris-HCl (pH 8.3), 5 mM $MgCl_2$, 50 mM KCl, 1 mM deoxy-NTPs, and 2.5 μM random hexamer. Then, 2 μL of the diluted cDNA product was mixed with 10 mM Tris-HCl (pH 8.3), 50 mM KCl, 4 mM $MgCl_2$, 0.025 U/μL Taq DNA polymerase (Takara Biochemicals, Osaka, Japan), and 0.2 μM each of upstream sense primer and downstream antisense primer in a final volume of 25 μL. The sense primer (5'-ATCAGAGCTCCGAGAAGCGGTACC-3') (SEQ ID NO: 7) and the antisense primer (5'-GTCCACT-TGCAGTGTTATCCTG-3') (SEQ ID NO: 8) were used for PCR amplification of hTGF-β1 mRNA. A sense primer (5'-TCAAGAACGAAAGTCGGACG-3') (SEQ ID NO: 9) and an antisense primer (5'-GGACATCTAAGGGCATCACA-3') (SEQ ID NO:. 10) to human 18S ribosomal RNA were used as an internal control. PCR was performed by a Thermal Cycler (Perkin Elmer, Foster, Calif.). The conditions for PCR were the first denaturation at 94° C. for 2 minutes; 30 cycles of denaturation at 94° C. for 1 minute, annealing at 58° C. for 1 minute, and elongation at 72° C. for 1 minute; and the last elongation reaction at 72° C. for 10 minutes. PCR products obtained using 18S rRNA as a primer were included in each reaction as an internal control. In order to confirm that genome DNAs were not amplified by PCR, control RT-PCR experiments with a primer set and without reverse transcriptase were performed. In any reaction, no products were amplified. For semi-quantitative analysis of mRNA, the numbers of cycles whereby PCR products were detectable on gels were compared among various samples. cDNAs by successively 10 times dilutions (100, 10, and 1 ng) were amplified. An increased amount of cDNAs enabled the detection of the PCR products at an earlier cycle stage. The amount of the PCR products corresponding to each of target mRNA linearly increased through 20 to 35 cycles. The assay of the PCR products was conducted using Bio Analyzer (Agilent).

(7) Statistical Analysis

Results are expressed as mean ±SEM. The significance of difference between the means was evaluated by Student's t test. p>0.05 was considered significant.

II. Results (1) Binding of Synthesized Py-Im Polyamide to Double-Stranded Oligonucleotide The binding to target sequences of GB1105 and GB1106 was examined by gel shift assay. Sense and antisense oligonucleotide having 11 bases containing each target sequence of Py-Im polyamide were prepared, annealed to prepare a double-stranded DNA to the target site, and incubated with each Py-Im polyamide. The obtained products were electrophoresed with polyacrylamide gel and the binding between Py-Im and the target sequence was examined. In both cases of GB1105 and GB1106, addition of Py-Im polyamide to double-stranded DNAs (DS) decreased the migration degree in comparison with lanes with DS only, suggesting that the DNAs were polymerized. Thus, the binding of DS to Py-Im was proved. The results are shown in FIG. 3.

(2) Inhibition Effects of GB1105 on Expression of TGF-β1 Messenger RNA

Cultured human mesangium cells from kidney were cultured and stimulated by adding 1×10–6 M of PMA (12-O-tetradecanoylphorbol-13-acetate). Then, Py-Im (GB1105) was added to the cells so as to examine the inhibition effects on expression of TGF-β1 messenger RNA.

The media for the cells were changed to serum-free media in sub-confluent condition and cultured for 24 hours. After addition of 1×10$^{-6}$ M of PMA and each concentration of Py-Im, the cells were cultured for 12 hours in serum-free condition. Messenger RNAs were separated from the cells by guanidium thiocyanate method, reverse-transcribed with avian myeloblastoma virus reverse transcriptase, and amplified by PCR method. The obtained PCR products were assayed by Agilent Bioanalyzer. Primers specific to TGFβ1 gene and 18S rRNA were prepared and subjected to PCR, and the expression of TGFβ1 gene was corrected with 18s.

The expression of TGFβ1 gene was increased by 20% through 1×10$^{-6}$ M of PMA stimulation, and inhibited by up to 50% at a density of 1×10$^{-6}$ M by addition of GB1105 (FIG. 4).

(3) Inhibition Effects of GB1106 on Expression of TGF-β1 Messenger RNA

Cultured human mesangium cells from kidney were cultured and stimulated by adding 1×10$^{-6}$ M of PMA (12-O-tetradecanoylpholbol-13-acetate). Then, Py-Im (GB1106)

was added to the cells so as to examine the inhibition effects on expression of TGF-β1 messenger RNA.

The media for the cells were changed to serum-free media in sub-confluent condition and cultured for 24 hours. After addition of $1\times10^{-6}$ M of PMA and each concentration of Py-Im, the cells were cultured for 12 hours in serum-free condition. Messenger RNAs were separated from the cells by guanidium thiocyanate method, reverse-transcribed with avian myeloblastoma virus reverse transcriptase, and amplified by PCR method. The obtained PCR products were assayed by Agilent Bioanalyzer. Primers specific to TGFβ1 gene and 1S rRNA were prepared and subjected to PCR, and the expression of TGFβ1 gene was corrected with 18s.

The expression of TGFβ1 gene was increased by 20% through $1\times10^{-6}$ M of PMA stimulation, and inhibited by up to 50% at a density of $1\times10^{-6}$ M by addition of GB1106 (FIG. 5).

INDUSTRIAL APPLICABILITY

A TGF-β gene expression inhibitor of the present invention is usable as a therapeutic agent for diseases associated with the production of TGF-β.

Sequence List Free Text

SEQ ID NO. 7 Sense primer
SEQ ID NO. 8 Antisense primer
SEQ ID NO. 9 Sense primer
SEQ ID NO. 10 Antisense primer

The invention claimed is:

1. A TGF-β gene expression inhibitor comprising a pyrrole imidazole polyamide represented by the following formula:

[Formula 1]

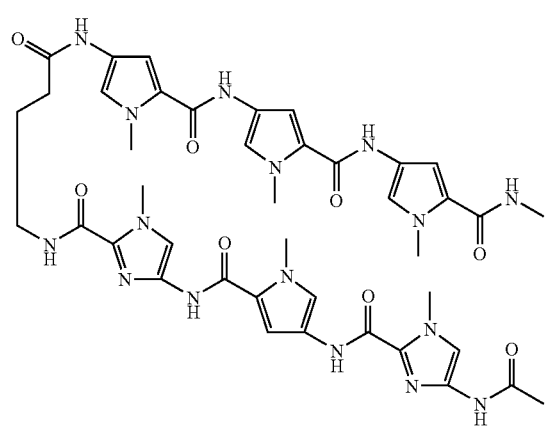

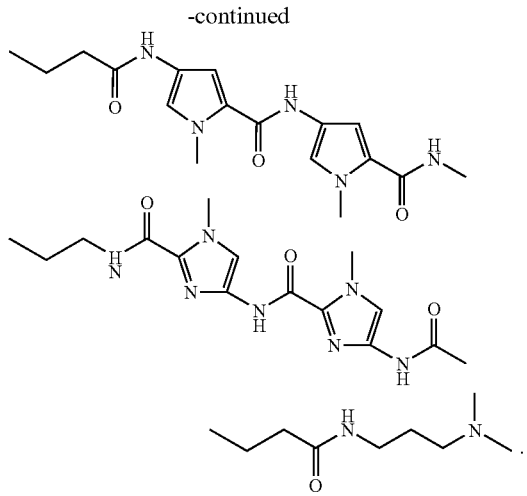

2. A TGF-β gene expression inhibitor comprising a pyrrole imidazole polyamide represented by the following formula:

[Formula 2]

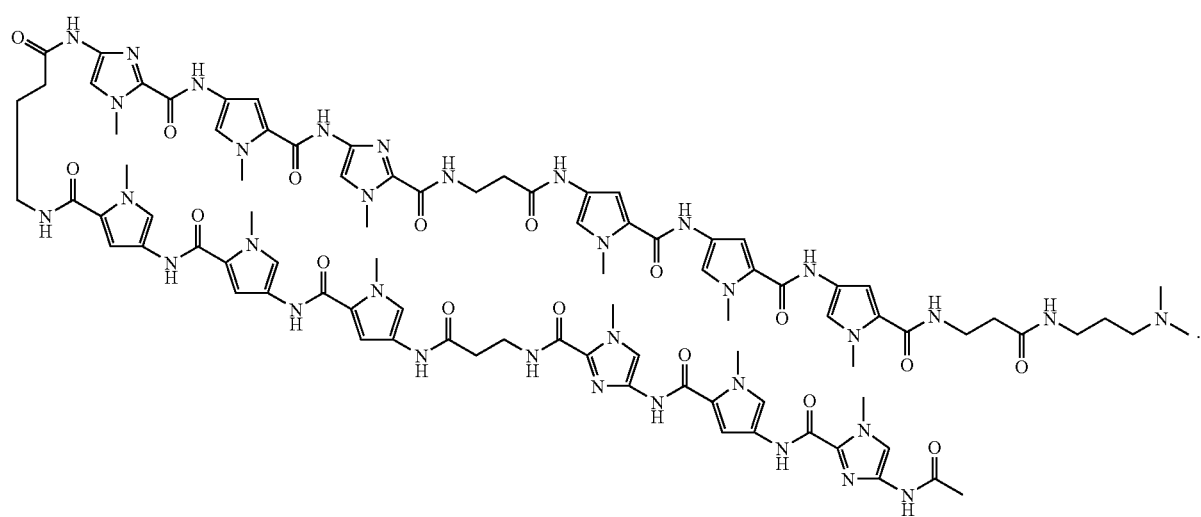

3. A pyrrole-imidazole polyamide represented by the following formulas:
[Formula 3]
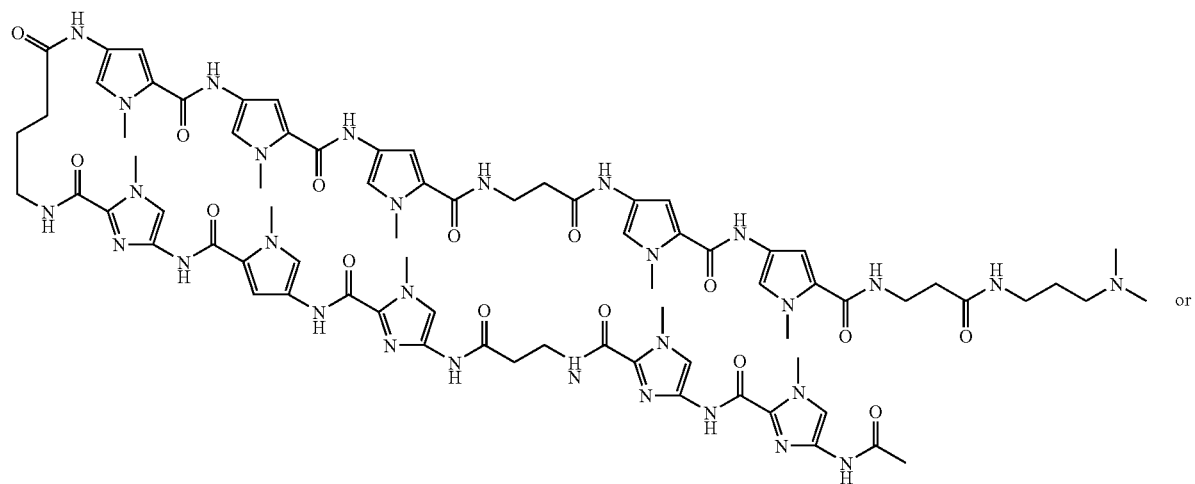
or
[Formula 4]
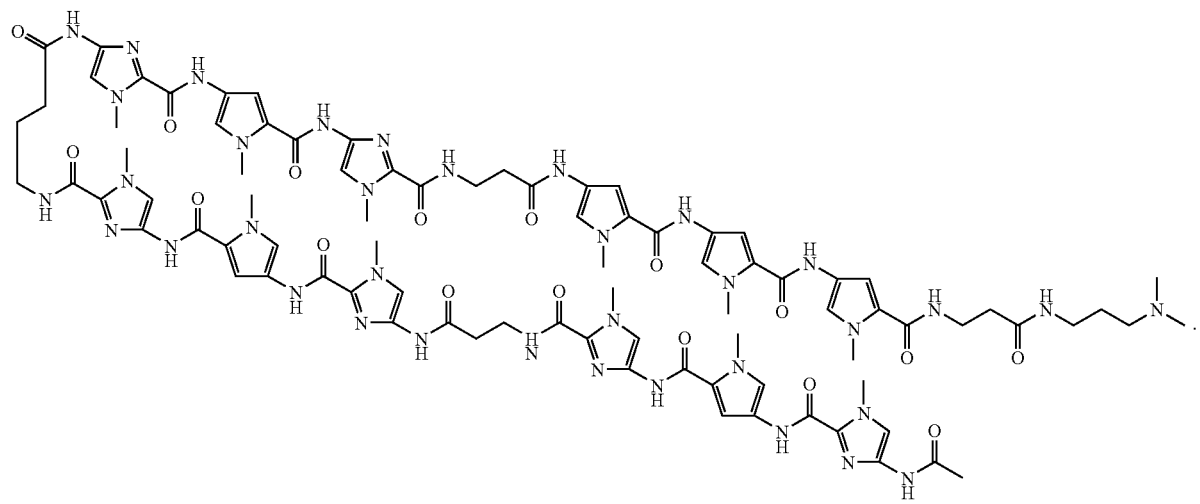
* * * * *